United States Patent
Peeters et al.

(10) Patent No.: US 10,434,280 B2
(45) Date of Patent: Oct. 8, 2019

(54) BIO HUE LAMP

(71) Applicant: SIGNIFY HOLDING B.V., Eindhoven (NL)

(72) Inventors: Martinus Petrus Joseph Peeters, Eindhoven (NL); Rémy Cyrille Broersma, Eindhoven (NL); Yue Jun Sun, Eindhoven (NL); René Theodorus Wegh, Eindhoven (NL); Dragan Sekulovski, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 85 days.

(21) Appl. No.: 15/558,396

(22) PCT Filed: Mar. 16, 2016

(86) PCT No.: PCT/EP2016/055696
§ 371 (c)(1),
(2) Date: Sep. 14, 2017

(87) PCT Pub. No.: WO2016/146688
PCT Pub. Date: Sep. 22, 2016

(65) Prior Publication Data
US 2018/0056027 A1    Mar. 1, 2018

(30) Foreign Application Priority Data
Mar. 19, 2015 (EP) ..................... 15159899

(51) Int. Cl.
*A61M 21/02* (2006.01)
*F21K 9/64* (2016.01)
(Continued)

(52) U.S. Cl.
CPC .......... *A61M 21/02* (2013.01); *A61N 5/0618* (2013.01); *F21K 9/64* (2016.08); *F21V 9/30* (2018.02);
(Continued)

(58) Field of Classification Search
CPC .......... A61M 21/02; A61M 2021/0083; A61M 2021/0044; H05B 33/0872; H05B 33/0854; F21K 9/64; F21V 9/30; A61N 5/0618; A61N 2005/0663; F21Y 2113/13; F21Y 2115/10
See application file for complete search history.

(56) References Cited

U.S. PATENT DOCUMENTS

2008/0231214 A1    9/2008 Kim et al.
2009/0303694 A1    12/2009 Roth et al.
(Continued)

FOREIGN PATENT DOCUMENTS

JP    2005063687 A1    3/2005
WO   WO2007116341 A1   10/2007
(Continued)

*Primary Examiner* — Mark Bockelman
(74) *Attorney, Agent, or Firm* — Meenakshy Chakravorty

(57) ABSTRACT

The invention provides a three-channel lighting apparatus with the option to support the human circadian rhythm. By choosing especially the blue LED and green phosphor, the range of biological activity that can be changed is optimized. By adjustment of the LED spectra a bigger range in melanopsin effectiveness factor, at the same CCT range (from daylight like CCT down to dimmed halogen), can be obtained.

15 Claims, 5 Drawing Sheets

(51) Int. Cl.
 *F21V 9/16* (2006.01)
 *H05B 33/08* (2006.01)
 *A61N 5/06* (2006.01)
 *F21V 9/30* (2018.01)
 *A61M 21/00* (2006.01)
 *F21Y 113/13* (2016.01)
 *F21Y 115/10* (2016.01)

(52) U.S. Cl.
 CPC ..... *H05B 33/0854* (2013.01); *H05B 33/0872* (2013.01); *A61M 2021/0044* (2013.01); *A61M 2021/0083* (2013.01); *A61N 2005/0663* (2013.01); *F21Y 2113/13* (2016.08); *F21Y 2115/10* (2016.08)

(56) References Cited

U.S. PATENT DOCUMENTS

| | | |
|---|---|---|
| 2010/0171441 A1 | 7/2010 | Schlangen et al. |
| 2011/0084614 A1 | 4/2011 | Eisele et al. |
| 2012/0069551 A1 | 3/2012 | Bues et al. |
| 2013/0140988 A1 | 6/2013 | Maxik et al. |
| 2014/0117877 A1 | 5/2014 | Mapel et al. |

FOREIGN PATENT DOCUMENTS

| | | |
|---|---|---|
| WO | WO2008069103 A1 | 6/2008 |
| WO | WO2008146219 A1 | 12/2008 |
| WO | WO2014009865 A1 | 1/2014 |
| WO | WO2015014936 A1 | 2/2015 |

BIO HUE LAMP

CROSS-REFERENCE TO PRIOR APPLICATIONS

This application is the U.S. National Phase application under 35 U.S.C. § 371 of International Application No. PCT/EP2016/055696, filed on Mar. 16, 2016, which claims the benefit of European Patent Application No. 15159899.2, filed on Mar. 19, 2015. These applications are hereby incorporated by reference herein.

FIELD OF THE INVENTION

The invention relates to a lighting apparatus for providing white light. The invention further relates to the use of such lighting apparatus to support the human circadian rhythm.

BACKGROUND OF THE INVENTION

Lighting solutions taking into account circadian rhythm aspects are known in the art. WO2008/146219, for instance, describes methods and systems for emitting light that can provide a desired light-induced physiological stimulus and a desired luminous stimulus. The light can be controlled to vary the physiological stimulus within a predetermined first range while maintaining the luminous stimulus within a predetermined second range that is useful for a number of self and/or space illumination applications. For example, an apparatus may include a controller for controlling the drive currents supplied to a plurality of light-emitting elements having different spectral characteristics, wherein the combination of currents is controlled such that the mixed light emitted is associated with the desired physiological and luminous stimuli.

WO 2015/014936 A1 discloses a lighting unit comprising a first light source, a second light source, a first wavelength converting, a second wavelength converting element, wherein the lighting unit further comprises a transport infrastructure configured to arrange the first light source, the second light source, the first wavelength converting element, and the second wavelength converting element in a first configuration or a second configuration by transport of one or more of these, wherein in the first configuration and the second configuration the lighting unit provides lighting unit light having substantially the same color point while having different color rendering indices. With such lighting unit, it is possible to switch between high CRI-low efficiency and low CRI-high efficiency at a given color temperature (or color point).

SUMMARY OF THE INVENTION

Critical to our sleep/wake cycle is melatonin, a hormone that promotes sleep during night time. During day time, natural daylight with high correlated color temperature (CCT; herein also indicated as "color temperature") and intensity suppresses melatonin production in the body and as a result energizes people, making them more awake and alert. At the beginning and end of the day the spectrum is shifted towards lower CCT and intensity levels, causing melatonin secretion.

Current high performance LED based lighting apparatus with tunable CCT are able to mimic different phases of daylight, i.e., changes in spectral power distribution and variations in CCT, to certain extend. However, it has been found that there is a further desire to improve lighting apparatus to better support the human circadian rhythm. Further, prior art lighting apparatus may need complicated solutions to be able to tune the color temperature such that the white light provided is close (enough) to the black body locus (BBL), or is only close to the BBL over a small CCT range. In addition, some of the prior art lighting systems provide a relative good tuneability, but they may show considerable variations in color fidelity (CIE-Ra) values over the tunable CCT range and consequently, for some settings, the color quality may become unacceptable. Finally, some of the prior art lighting systems are able to tune the color of the white light over a broader CCT range, with acceptable color fidelity (CIE-Ra) values, but fail to optimize the spectral power distribution of the light with regard to supporting the human circadian rhythm, i.e., suppressing or supporting melatonin production.

Hence, it is an aspect of the invention to provide an alternative lighting apparatus, which preferably further at least partly obviates one or more of above-described drawbacks. Such lighting apparatus especially may be used for supporting the human circadian rhythm, may be especially tunable in the melanopsin sensitive wavelength range, may be especially tunable over a large color temperature range, or may have sufficiently high CRI values over a substantial part of the variable correlated color temperature range. Alternatively or additionally, the lighting apparatus may especially be used for maximizing alertness when desired, such as being configured to maximize alertness in predetermined conditions and/or for not disrupting the human circadian rhythm in other predetermined conditions.

Next to the commonly known cones and rods, the human eye has melanopsin containing photoreceptors, affecting melatonin secretion, which are sensitive in a specific wavelength range. The relative spectral sensitivity for photopic and melanopic receptors are provided in FIG. 1. If the spectral power in the melanopic wavelength range is absent or low, melatonin hormone production will be enabled to promote sleep. If the spectral power in the melanopic range is high enough, melatonin production will be suppressed and consequently we will become more alert. The effectiveness of suppressing melatonin production can be expressed in terms of the melanopsin effectiveness factor (MEF). This factor is calculated by multiplying the spectral power distribution of the light emitted by a lighting apparatus (SPD ($\lambda$)) with the melanopic sensitivity function (m($\lambda$)) divided by the product of SPD($\lambda$) and the photopic sensitivity (V($\lambda$)), normalized by the areas of m($\lambda$) and V($\lambda$), see equation 1 (and see also FIG. 1).

$$MEF = ([\sum V(\lambda)]/[\sum m(\lambda)]) \cdot [\sum (SPD(\lambda) \cdot m(\lambda))]/[\sum (SPD(\lambda) \cdot V(\lambda))] \quad \text{(equation (1))}$$

This can be simplified to $$MEF = 1.22 \cdot [\sum (SPD(\lambda) \cdot m(\lambda))]/[\sum (SPD(\lambda) \cdot V(\lambda))] \quad \text{(equation (2))}$$

as $$MEF = 1.22 \cdot \frac{\sum_{\lambda=380nm}^{\lambda=780nm} (SPD(\lambda) \cdot m(\lambda))}{\sum_{\lambda=380nm}^{\lambda=780nm} (SPD(\lambda) \cdot V(\lambda))}$$

Hence, the above indicated summations are over the visible range of 380-780 nm.

Current high performance LED based lighting apparatus appear to show a melanopsin effectiveness change by a factor of about 3 over the 2200K to 5700K range (i.e. a correlated color temperature range of 3500 K). It has been found that it is advantageous for supporting the circadian rhythm that the melanopsin effectiveness (MEF) should be low at low color temperatures and may especially be high at higher color temperatures. The MEF value can also be optimized for a particular activity, e.g. low MEF value in the evening before going to sleep and high MEF value in the morning while waking up. Also applying high MEF values may be useful for (temporarily) increasing alertness.

Herein, we propose a three-channel lighting apparatus with the option to support the human circadian rhythm. By choosing especially a blue LED and a green phosphor ("luminescent material"), the range of biological activity that can be induced by the light emitted by the three-channel lighting apparatus is optimized. By adjustment of intensities of the LEDs a bigger range in melanopsin effectiveness factor, at the same CCT range (from daylight down to dimmed halogen), can be obtained. In this way a lighting apparatus can be made that (better) supports the circadian rhythm and/or influences the level of alertness. The proposed lighting apparatus can produce light covering a range of a factor of about 4 in melanopsin effectiveness at the same photopic light level, i.e., (substantially) without adjusting the photopic light flux. In addition, the spectral power of the lighting apparatus can be adjusted at low CCT values to (further) reduce the MEF value. Notably, the biological activity induced by the lighting apparatus is a product of amount of light and spectral content (e.g. the melanopic flux). In a specific embodiment, the lighting apparatus contains two green/blue channels, combined with a red channel (3-channels in total). By choosing the blue LED/green phosphor combination for each of the green/blue channels, a lighting apparatus can be made with optimal melanopsin activation for the high CCT settings, and a very low melanopsin activation level for the low CCT setting. By using a smart driver (control unit), the lighting apparatus can automatically follow the day/night rhythm including a BBL-dimming characteristic. Both the spectral distribution of the light and the light level of this light of the lighting apparatus can be adjusted.

Hence, the invention especially provides in a first aspect three (different types of) light sources, which are independently controllable in intensity, wherein the first light source is configured to provide blue light and one or more of green and yellow light; a second light source is configured to provide blue light, other than the blue light of the first light source and green light; and a third light source is configured to provide red light. By controlling the intensities of the light sources, a correlated color temperature range of at least 2000 K, such as e.g. between at least 2000-4000 K, even more especially over a range of at least 3000 K, such as e.g. between at least 2000-5000 K, can be achieved, with a CRI of at least 80, especially within about 15 SDCM (standard deviation of color matching) from the BBL (black body locus), more especially within about 10 SDCM from the BBL, even more especially within about 5 SDCM from the BBL, and having a melanopsin effectiveness range (MEF) of especially at least about 3.5, such as even at least about 4. Especially, this may be achieved with the blue light of the light sources having a dominant wavelength below 490 nm, with the dominant wavelength of the blue light of the first light source being smaller than the dominant wavelength of the blue light of the second light source. Hence, in a relative simple way a lighting apparatus is provided that is intended to support the biorhythm, and is herein therefore also indicated as "bio hue lamp" or "bio hue lighting apparatus". Especially, the lighting apparatus is configured to provide a melanopsin effectiveness range per temperature unit of at least 0.915/1000 K, such as at least 0.920/1000 K. For instance, a MEF range of 3.5 over a temperature of 3800 K (like 2400-6200 K) would provide a melanopsin effectiveness range per temperature unit of 0.921/1000 K.

Especially, the invention provides a lighting apparatus configured to provide white light with a variable correlated color temperature, wherein the lighting apparatus comprises: (a) a first light source configured to provide first light source light, wherein the first light source light comprises blue light having a first light source dominant wavelength selected from the range of 400-460 nm, especially in the range of 420-460, such as in the range of 430-460 nm, like 430-450 nm, like 440-450 nm, wherein the first light source is configured to irradiate a first luminescent material with said first light source light, wherein the first luminescent material is configured to convert part of the first light source light into first luminescent material light, wherein the first luminescent material light comprises one or more of green and yellow light, and wherein the first luminescent material light has a first luminescent material dominant wavelength; (b) a second light source configured to provide second light source light, wherein the second light source light comprises blue light having a second light source dominant wavelength selected from the range of 450-490 nm, such as 460-490 nm, wherein the second light source is configured to irradiate a second luminescent material with second light source light, and wherein the second luminescent material is configured to convert part of the second light source light into second luminescent material light, wherein the second luminescent material light comprises one or more of green and yellow light, and wherein the second luminescent material light has a second luminescent material dominant wavelength; (c) a third light source configured to provide red light source light; and (d) a control unit, configured to independently control the first light source, the second light source and the third light source, to provide said white light having a variable correlated color temperature, wherein said white light comprise one or more of (a) said first light source light, said first luminescent material light, and optionally said red light source light, and (b) said second light source light, said second luminescent material light, and (optionally) said red light source light; wherein the second light source dominant wavelength>first light source dominant wavelength, and wherein especially the first luminescent material dominant wavelength>second luminescent material dominant wavelength.

Especially, such lighting apparatus may be used for providing white light tunable over a correlated color temperature range of at least about 2000 K, especially for supporting bio rhythm. It also appears that such lighting apparatus may have a first melanopsin effectiveness at a first correlated color temperature and a second melanopsin effectiveness at a second correlated color temperature, wherein the second correlated color temperature is larger than the first correlated color temperature, and wherein the ratio of the second melanopsin effectiveness to the first melanopsin effectiveness is equal to or larger than 3.5. Hence, at high correlated color temperatures melatonin production in a human may be suppressed and at low correlated color temperatures the melanopsin-containing photoreceptors may e.g. be less activated and consequently melatonin production in a human may be less suppressed, or even not suppressed at all. On the other hand, in a specific embodiment early in the morning the color temperature may be chosen to be relatively low (but increasing), while the MEF value may be relatively high (and increasing), to facilitate waking up. Hence, the color temperatures just before bed time and early in the morning may substantially be the same, whereas the MEF value may differ.

Hence, the lighting apparatus is in an embodiment especially configured to provide at least two different types of white light: a first white light having a high correlated color temperature and a second white light having a low correlated color temperature, wherein the spectral overlap with the melanopic sensitivity curve may especially be smaller for the first white light than for the second white light.

The term white light herein, is known to the person skilled in the art. It especially relates to light having a correlated color temperature (CCT) between about 2000 K and 8000 K, especially in the range of about 2700 K and 6500 K, such as in the range of 2000-5700 K, and especially within about 15 SDCM (standard deviation of color matching) from the BBL (black body locus), especially within about 10 SDCM from the BBL, even more especially within about 5 SDCM from the BBL. Herein, as indicated above, the lighting apparatus may especially have a variable correlated color temperature over at least about 2000 K such as e.g. between at least about 2000-4000 K, even more especially at least over a range of at least about 3000 K, such as e.g. between at least about 2000-5000 K, or even variable over a correlated color temperature range of at least about 2000-5700 K.

The light sources are especially solid state light sources. Hence, in a specific embodiment, the light sources comprise solid state LED light sources (such as a LED or laser diode). The term "light source" may also relate to a plurality of light sources, such as 2-20 (solid state) LED light sources. Hence, the term LED may also refer to a plurality of LEDs.

Both the first light source and the second light source are configured to provide blue light, especially with a difference in dominant wavelengths in the range of about 15-30 nm, such as at least about 20 nm (see further also below). The third light source is configured to provide red light.

Hence, in embodiments (directly) downstream from the red light source substantially no blue light may be perceived, even when the red light source is based on conversion of blue light. For phosphor converted red LEDs the amount of blue light leakage should be low (otherwise a CCT as low as 2000K cannot be made), and if any, especially in the 400-460 nm wavelength range (low contribution to the MEF value).

Hence, in an embodiment the third light source may comprise a third solid state light source configured to provide third solid state light source light, wherein the third solid state light source light comprises blue light, wherein the third solid state light source is configured to irradiate a third luminescent material with third solid state light source light, and wherein the third luminescent material is configured to convert (at least) part of the third solid state light source light into third luminescent material light, wherein the third luminescent material light comprises red light. The third luminescent material may in principle be any red luminescent material excitable by the third solid state light source, such as inorganic phosphors, like a divalent europium based nitride phosphor and/or a quantum dot based phosphor, or organic phosphors, or a combination of two or more different phosphors. Hence, the third light source may optionally also provide light source light at a longer (or shorter) wavelength than blue light. However, especially substantially all visible light generated by the third light source is absorbed (and at least partially converted) into third luminescent material light in those embodiments wherein the third light source is radiationally coupled with a third luminescent material. Hence, especially at least 90% of the total power (W) in the visible part of the spectrum of the red light source is in the red, even more especially at least 95% of the total power in the visible part.

The term "radiationally coupled" especially means that the light source and the luminescent material are associated with each other so that at least part of the radiation emitted by the light source is received by the luminescent material (and at least partly converted into luminescence). Thus, the first light source is especially radiationally coupled with the first luminescent material and the second light source is especially radiationally coupled with the second luminescent material. Likewise, when a red luminescent material is applied for the third (solid state) light source, the third (solid state) light source is especially radiationally coupled to the third luminescent material.

Luminescent materials of specific interest are inorganic luminescent materials, even more especially (independently) selected form the classes of sulfides, nitrides and oxynitrides. Here below, first a number of possible red luminescent materials are discussed, especially for application in/with the third light source.

A class of relevant luminescent materials include the MD:Eu class (herein also indicated as the (Sr,Ba,Ca)(Se,S): Eu class), which is the class of alkaline earth chalcogenide systems. M is especially selected from the group of earth alkaline elements (Mg, Ca, Sr, Ba), and D is especially selected from the group of S and Se. The materials within this class have a cubic rock salt crystal structure. Examples of members within this class are SrS:Eu, CaS:Eu, CaSe:Eu, etc.

A further class of relevant luminescent materials includes the $M_2Z_5N_8$:Eu class (herein also indicated as the $Sr_2Si_5N_8$:Eu class), which is the class of nitridosilicate systems. M is especially selected from the group of earth alkaline elements (Mg, Ca, Sr, Ba), especially at least Sr, and Z is especially selected from the group of Si, Ge, Ti, Hf, Zr, Sn, especially at least Si. The materials within this class have an orthorhombic crystal structure. An example of a member within this class is $SrCaSi_5N_8$:Eu.

In yet another embodiment, the luminescent material comprises a luminescent material of the class of $M_2SiF_6$:Mn (tetravalent manganese), wherein M is especially selected from the group consisting of Rb and K. Hence, in a further embodiment the luminescent material may comprise $M'_xM_{2-2x}AX_6$ doped with tetravalent manganese. Relevant alkaline cations (M) are sodium (Na), potassium (K) and rubidium (Rb). Optionally, also lithium and/or cesium may be applied. In a preferred embodiment, M comprises at least potassium. In yet another embodiment, M comprises at least rubidium. The phrase "wherein M comprises at least potassium" indicates for instance that of all M cations in a mole $M'_xM_{2-2}AX_6$, a fraction comprises $K^+$ and an optionally remaining fraction comprises one or more other monovalent (alkaline) cations (see also below). In another preferred embodiment, M comprises at least potassium and rubidium. Optionally, the $M'_xM_{2-2x}AX_6$ luminescent material has the hexagonal phase. In yet another embodiment, the $M'_xM_{2-2x}AX_6$ luminescent material has the cubic phase. Relevant alkaline earth cations (M') are magnesium (Mg), strontium (Sr), calcium (Ca) and barium (Ba), especially one or more of Sr and Ba. In an embodiment, a combination of different alkaline cations may be applied. In yet another embodiment, a combination of different alkaline earth cations may be applied. In yet another embodiment, a combination of one or more alkaline cations and one or more alkaline earth cations may be applied. For instance, $KRb_{0.5}Sr_{0.25}AX_6$ might be applied. As indicated above, x may be in the range of 0-1, especially x<1. In an embodiment, x=0.

Another class of relevant luminescent materials includes the $MGD_3N_4$:Eu class (herein also indicated as the $SrLiAl_3N_4$:Eu class), which is the class of nitridoaluminate systems. M is especially selected from the group of earth alkaline elements (Mg, Ca, Sr, Ba), especially at least Sr. D is especially selected from the group of B, Al, Ga, Sc, especially at least Al, and G is especially selected from the group of alkaline elements (such as Li, Na, K, etc.), especially at least Li. The materials within this class have a triclinic potassium lithium plumbate type crystal structure or a tetragonal sodium lithium silicate type crystal structure. An example of a member within this class is $SrLiAl_3N_4$:Eu.

Especially good optical results may be obtained, when the red luminescent material is selected from the group consisting of the class of $M_2Si_5N_8$:Eu and the class of $MLiAl_3N_4$:Eu, wherein M is independently selected from the group consisting of Ca, Mg, Sr, and Ba, especially at least one or more of Ca and Sr, yet even more especially at least Sr.

The term "class" herein especially refers to a group of materials that have the same crystallographic structure. Further, the term "class" may also include partial substitutions of cations and/or anions. For instance, in some of the above-mentioned classes Al—O may partially be replaced by Si—N (or the other way around). Hence, in yet a further embodiment the red luminescent material is selected from the group consisting of $(Ba,Sr,Ca)_2Si_{5-x}Al_xN_{8-x}O_x$:Eu, wherein x is in the range of 0-4, especially equal to or lower than 1, such as 0, and $(Ca,Sr)LiAl_3N_4$:Eu. $(Ba,Sr,Ca)_2Si_{5-x}Al_xN_{8-x}O_x$:Eu and similar systems are amongst others described in WO2006072918/US20130240943, which are incorporated herein by reference. $(Sr,Ca)LiAl_3N_4$:Eu and similar systems are amongst others described in WO2013175336A1, which is incorporated herein by reference. In even yet a more specific embodiment, the red luminescent material comprises one or more of $(Sr,Ca)_2Si_5N_8$:Eu, and $SrLiAl_3N_4$:Eu.

In a specific embodiment, the third luminescent material comprises $MAlSiN_3$:Eu(II) (i.e. a divalent europium doped alkaline earth aluminum silicon nitride), wherein M comprises one or more elements selected from the group consisting of barium (Ba), strontium (Sr) and calcium (Ca), especially M comprises at least one or more of calcium and strontium, especially at least strontium. The term "Eu(II)" indicates divalent europium. The term ":Eu" and similar terms indicate that the inorganic material is doped with Eu, or other elements (ions), as known in the art.

In yet another embodiment the third light source comprises a third solid state light source configured to provide red third solid state light source light (such as a red emitting LED, or a red emitting OLED). Of course, also combinations of different types of red light sources may be applied.

The first light source and the second light source are each independently also especially selected from the group of solid state light sources, such as a LED or laser diode. Also for the first and the second light source applies of course that the term "light source" may relate to a plurality of light sources, such as 2-20 (solid state) LED light sources. The first and the second light source are especially configured to address with their respective light source light different luminescent materials, with the first luminescent material being addressed by the first light source and the second luminescent material being addressed by the second light source. Hence, the different luminescent materials (optionally also including the third luminescent material) are predominantly irradiated by the respective light source. Especially, each luminescent material receives for more than 50% of the total irradiated power, especially more than 80% of the irradiated power, radiation from the respective light source. Hence, the respective light sources are radiationally coupled with their respective luminescent materials (see also above).

Therefore, in a specific embodiment the lighting apparatus comprises a first LED package comprising the first light source and the first luminescent material and/or a second LED package comprising the second light source and the second luminescent material. Alternatively or additionally, the lighting apparatus may thus also comprise a third LED package comprising the third solid state light source and the third luminescent material. Hence, in the former embodiment, downstream of the packages (a) blue light and one or more of green light and yellow light and/or (b) blue light and green light will be perceived, whereas in the latter embodiment (directly) downstream from the package substantially only red light will be perceived. The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

Especially good results were obtained when the blue light of both first and second light sources is substantially below 490 nm, such as equal to or smaller than 475 nm. This wavelength is about the maximum of the melanopic curve (~490 nm). Hence, in a specific embodiment the second light source dominant wavelength ≤490 nm, even more especially ≤475 nm. As mentioned above, the first light source dominant wavelength is smaller than the second light source dominant wavelength, and thus the first light source dominant wavelength in this embodiment is by definition <490 nm. By choosing these wavelengths, this allows the lighting apparatus to be selected between two main options, i.e. a first option with a high correlated color temperature with blue light relatively close to the melanopic curve maximum, i.e. enhancing alertness/awakeness, and an a second option with a second correlated color temperature with blue light more remote from the melanopic curve maximum, i.e. addressing less the melanopsin-containing photoreceptors in the eye and therefore relatively less suppressing melatonin production (relative to the first option).

In a more specific embodiment, the first light source light has a dominant wavelength selected from the range of 430-450 nm, and the second light source light has a dominant wavelength selected from the range of 450-475 nm. Further, especially the difference in dominant wavelengths (of the first light source light and the second light source light) is in the range of at least 10 nm, especially in the range of 15-30 nm. In such embodiment, especially the high melanopsin effectiveness ratio change may be obtained.

With respect to the luminescent materials for especially the first light source and the second light source (but also for the third light source, see also above), in principle any suitable luminescent material may be chosen, being inorganic or organic, or combinations of inorganic and organic phosphors (see also above).

However, in a specific embodiment the first luminescent material and the second luminescent material are selected from the group of cerium doped garnet luminescent materials. Alternatively or additionally, one or more of the first luminescent material and the second luminescent material are selected from the group of quantum dot luminescent materials. Hence, the luminescent materials may also (each independently) be selected from the group consisting of luminescent oxide materials.

Especially good results were obtained when the first luminescent material is configured to emit in the green-yellow and the second luminescent material is configured to emit in the green. Hence, in a specific embodiment wherein the first luminescent material light of the first luminescent material has a dominant wavelength selected from the range of 550-590 nm, and wherein the second luminescent material light of the second luminescent material has a dominant wavelength selected from the range of 520-550 nm. For these type of applications, especially suitable may be garnet type of luminescent material (see also above).

Hence, in a further embodiment the first luminescent material and the second luminescent material comprise $A_3B_5O_{12}:Ce^{3+}$, wherein A is selected from the group consisting of Y, Gd, Tb and Lu, and wherein B is selected from the group consisting of Al, Ga and Sc. The first luminescent material and/or second luminescent material may (thus) comprise a garnet material. Especially the first luminescent material and/or second luminescent material may comprise a luminescent ceramic. The garnet material, especially the ceramic garnet material, is herein also indicated as "luminescent material". The luminescent material comprises a $A_3B_5O_{12}:Ce^{3+}$ (garnet material), wherein A is especially selected from the group consisting of Sc, Y, Tb, Gd, and Lu, wherein B is especially selected from the group consisting of Al, Sc and Ga. More especially, A comprises one or more of yttrium (Y), gadolinium (Gd) and lutetium (Lu), and B comprises aluminum (Al). Such garnet may be doped with cerium (Ce), and optionally with other luminescent species such as praseodymium (Pr). In a specific embodiment, B consists of about 40% or more of Al and 60% or less of Ga. Especially, B comprises aluminum (Al), however, B may also partly comprise gallium (Ga) and/or scandium (Sc) and/or indium (In), especially up to about 20% of Al, more especially up to about 10% of Al may be replaced (i.e. the A ions essentially consist of 90 or more mole % of Al and 10 or less mole % of one or more of Ga, Sc and In); B may especially comprise up to about 10% gallium. In another variant, B and O may at least partly be replaced by Si and N. As indicated above, the element A may especially be selected from the group consisting of yttrium (Y), gadolinium (Gd), terbium (Tb) and lutetium (Lu). Especially, for the first luminescent material the mole percentage of Y relative to A is larger than for the second luminescent material, and for the second luminescent the mole percentage of Lu relative to A is larger than for the first luminescent material. Hence, for instance both the first luminescent material and the second luminescent material may comprise Y and Lu (i.e. A elements), but the former comprises more Y than the latter and the latter comprises more Lu than the former. In this way the former luminescent material has a dominant wavelength at a longer wavelength than the latter luminescent material. Instead of or in addition to LuAG one may also apply GaYAG (i.e. $Y_3Ga_5O_{12}:Ce^{3+}$). Hence, mixtures of such luminescent materials may be applied, but also mix crystals may be applied, such as $(YLu_2Ga_4AlO_{12}:Ce^{3+})$.

The luminescent materials described herein are especially indicated with their chemical formulas. Even thought the elements are indicated, the presence of impurities and/or other phases is not excluded. The luminescent material ("phosphor") may also include impurities, like one or more of halogen impurities and metal impurities. The luminescent material, may next to the one or more luminescent materials as defined herein, also include other phases, like one or more of the—already indicated (remaining—flux material, remaining starting material(s) and one or more phases that are also formed during synthesis of the one or more (respective) luminescent materials. Likewise, the luminescent material may also include other phases, like one or more of the—already indicated (remaining)—flux material, remaining starting material(s) and one or more phases that are also formed during synthesis of the one or more (respective) luminescent materials. In general, the weight percentage of such other phase(s) will be below about 10 wt. % (relative to the total weight of the luminescent material. This is known in the art.

As indicated above, the luminescent material may also include impurities. This is known in the art. Hence, in embodiments chemical formulas like $MAlSiN_3:Eu(II)$, etc., do not exclude the presence of impurities, for instance up to a total of about 500 ppm, especially up to about 200 ppm, even more especially up to about 100 ppm. Hence, even though the chemical formula does not indicate the presence of impurities, impurities that may (nevertheless) be present can for instance be selected from the group consisting of Li, Na, K, Sc, Y, Ti, Zr, V, Nb, Cr, Mo, Mn, Fe, Ru, Co, Rh, Ni, Pd, Cu, Zn, V, C, N, O, F, Al, Si, P, S, Cl, Ga, Ge, Se, Br, Lu, La, Ce, Pr, Nd, Sm, Eu, Gd, Tb, Dy, Ho, Er, Tm, Yb, Hf, Ta, W, Re, Os, Ir, Pt, Tl, Pb, and Bi. Here, impurities are listed. When for instance the chemical formula indicates the availability of Li or Eu, these are—even when available in small amounts not considered as impurities. Hence, e.g. in $MAlSiN_3:Eu(II)$, Eu is not an impurity, but $MAlSiN_3:Eu(II)$ may include e.g. 150 ppm Hf or Na or Mg (as impurity/impurities).

Further, the luminescent material may include one or more of scattering particles and a halide salt.

Further, the lighting apparatus may comprise a control unit. This control unit is especially configured to independently control the first light source, the second light source and the third light source, to provide said white light having a variable correlated color temperature. Hence, the intensities of these respective light sources may be tuned to vary the correlated color temperature (and MEF), e.g. in the above indicted ranges, e.g. by continuously adjusting. In this way, white light is provided comprising one or more of (a) said first light source light and said first luminescent material light and especially also said red light source light, and (b) said second light source light and said second luminescent material light and especially also said red light source light. In a first extreme, the white light comprises said red light and only said first light source light and said first luminescent material light, which may be a low correlated color temperature white light (with low MEF). In another extreme, the white light may comprise said red light and only said second light source light and said second luminescent material light, which may be a high correlated color temperature white light (with high MEF). Hence, the lighting apparatus may be used for providing white light tunable over a correlated color temperature range of at least 2000 K, and for providing a variable spectral power distribution in the blue range of the spectrum as function of the correlated color temperature.

Especially, the control unit is configured to control the first light source, the second light source and the third light source. Especially, the control unit is thus configured to control the intensity of the first light source light, the second light source light and the third light source light. The control unit can especially control the light sources independently, though especially the two or more light sources together provide the white light (of the lighting apparatus. Further, especially the control unit is configured to control the first light source, the second light source and the third light source as function of one or more of a time signal and an ambient light sensor. In this way, the lighting apparatus may e.g. automatically adjust the correlated color temperature. However, in yet a further embodiment the control unit may also be configured to control the light sources as function of a user input value. For instance, one may desire to adjust the correlated color temperature or correlated color temperature scheme, for example to prepare for a jetlag or to recover from a jetlag (smoothly). In yet a further embodiment, the lighting apparatus further comprising a fourth light source configured to provide fourth light source light, comprising cyan light.

In yet a further embodiment, the control unit is further configured to control the melanopsin effectiveness factor (MEF) of the white light. In this way, the white light may be tuned to the desired MEF, e.g. a high factor during the day, and a decreasing factor when approaching bed time. The control unit may further especially also be configured to control the melanopsin effectiveness factor (MEF) as function of the correlated color temperature of the white light (and/or of the day time).

The lighting apparatus may further include a user interface. The user interface may be used to control (via the control unit) for instance one or more of the correlated color temperature, a color temperature scheme, an intensity of the white light, in input value related to the MEF, etc. The input value related to MEF may e.g. include input value like "bed time" (thus reducing MEF), "wake up" (increasing MEF), "increase alertness" (increasing MEF), "relax" (decreasing MEF), etc. etc. The user interface can be included in a remote control, such as a classical remote control, substantially only suitable for controlling the lighting apparatus. However, the user interface may also be included in a smart device, such as a mobile phone or other portable device including an app as user interface. The user interface may communicate wired or wireless, especially wireless, with the control unit. Hence, the user interface and the control unit are especially functionally connected.

The lighting apparatus may be part of a lighting system, wherein the lighting apparatus may be functionally connected to one or more other devices, including one or more other lighting apparatus. Hence, the invention also provides a lighting system comprising one or more, especially a plurality, lighting apparatus. For instance, the MEF value may be chosen by the control unit as function of the day time, with e.g. a low MEF before sleeping and a high MEF to get awake, or shortly after lunch. Alternatively or additionally, the MEF value may be selected in dependence of a human activity (or inactivity). Further, the MEF value may be selected as function of location, e.g. a relative higher MEF in a control room, or part of a control room, and a lower MEF at e.g. an relax area. Further, optionally or additionally, the MEF may be selected as function of a sensor, wherein the sensor is configured to sense human activity and/or human alertness. For instance, when a human starts falling asleep at a location and/or time where alertness is needed, the MEF value may be increased (when driving a car or other vehicle like a coach, a train, a truck, etc.; in a control room, etc. etc.).

In this way, with the light of the lighting apparatus one may change the way one feels himself or herself. With hue, one may get better control over the light and light impact on a person, as it may influence the mood and/or set the ambience.

The terms "violet light" or "violet emission" especially relates to light having a wavelength in the range of about 380-440 nm. The terms "blue light" or "blue emission" especially relates to light having a wavelength in the range of about 440-495 nm (including some violet and cyan hues). In the present invention, blue light is especially related to light having a wavelength in the range of 400-495 nm. The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component. The terms "visible", "visible light" or "visible emission" refer to light having a wavelength in the range of about 380-780 nm.

The lighting apparatus may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, green house lighting systems, horticulture lighting.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

Figure 1:
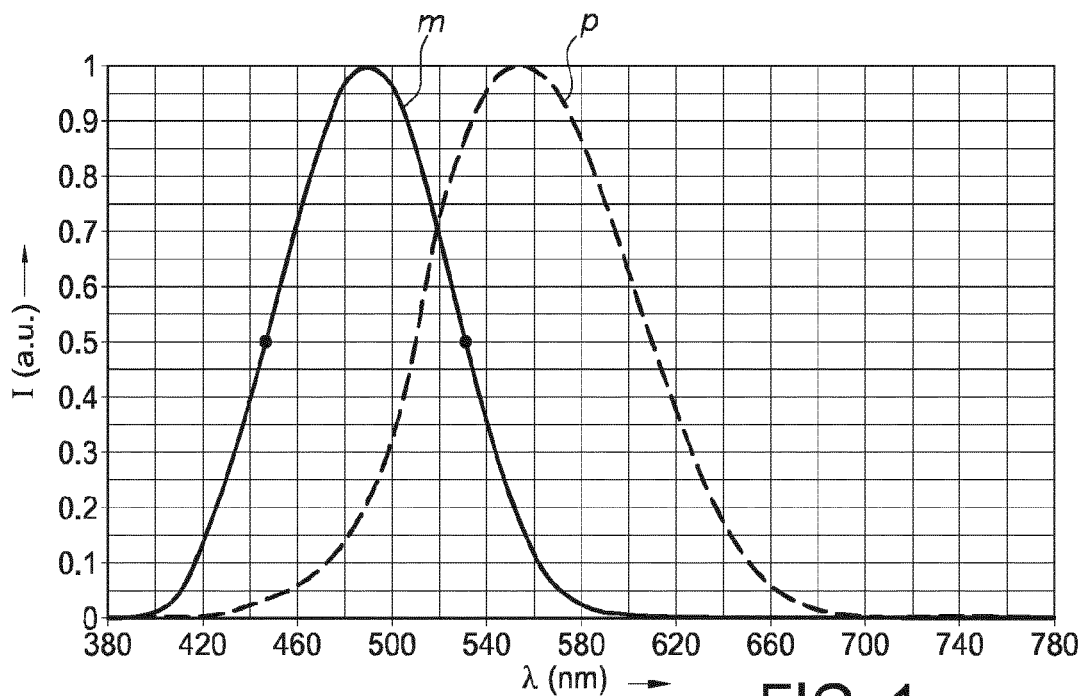
FIG. 1 shows the melanopic (solid line) (curve m) and photopic (dashed line) (curve p) human eye normalized sensitivity functions (R. J. Lucas, et al., Measuring and using light in the melanopsin age, Trends in Neurosciences, Volume 37, issue 1, January 2014, pp 1-9; http://www.sciencedirect.com/science/article/pii/S0166223613001975)

FIG. 1 shows the relative melanopic (m) and photopic (p) human eye sensitivity functions. The maximum sensitivity for the melanopic function is at 490 nm, the full width half maximum values are at 447 nm and 531 nm.

Figure 2:
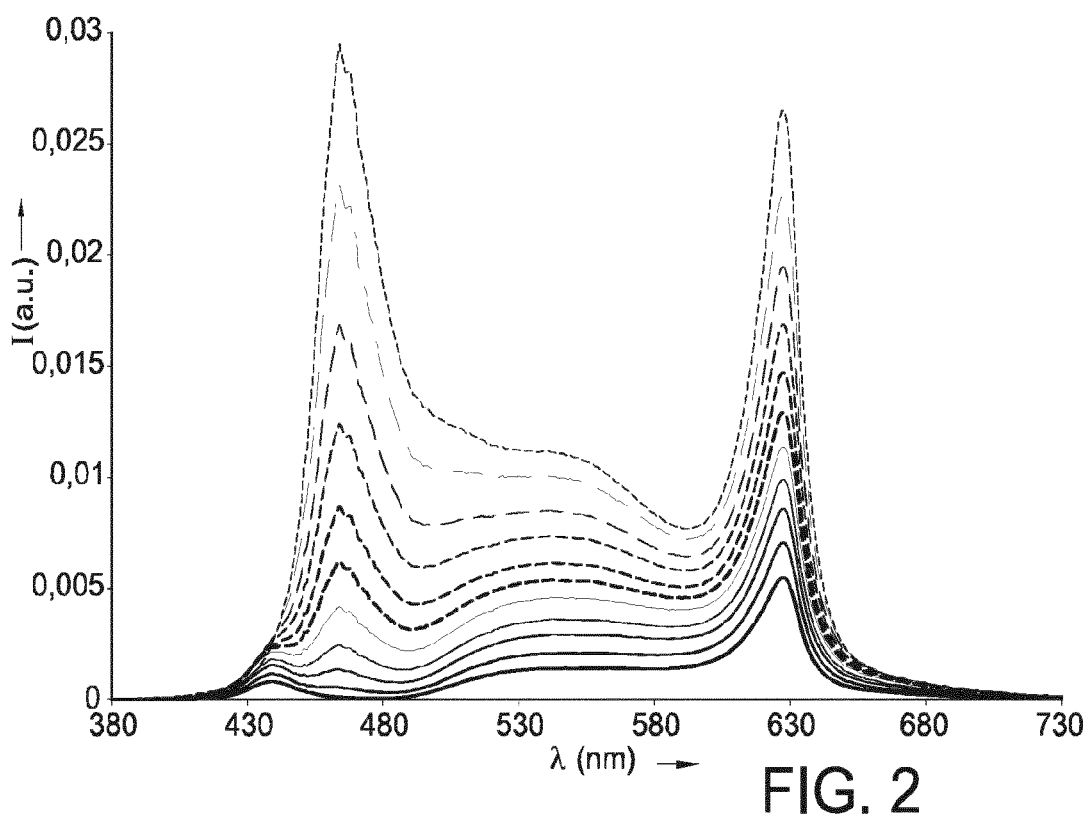
FIG. 2 shows an example of the tuning of the emission spectrum and thereby the correlated color temperature with an embodiment of the lighting apparatus.

FIG. 2 shows an example of the tuning of the emission spectrum and thereby the correlated color temperature with an embodiment of the lighting apparatus. Here, an embodiment was used with a blue LED with dominant wavelength at 440 nm, with YAG:Ce$^{3+}$, a blue LED with dominant wavelength at 462 m, with LuAG:Ce, and with a red LED with a dominant wavelength at 613 nm. The lowest curve (solid curve), has a relative high red contribution, and a relative low blue contribution, with the blue contribution at lower wavelengths, which is the relative warm white light. The highest curve has a relative high blue contribution, which blue contribution has shifted to a wavelength closer to the melanopic maximum (relative to the lower curves). Hence, this is relative cool white light, with a higher MEF value than the lower curves.

Figure 3A:
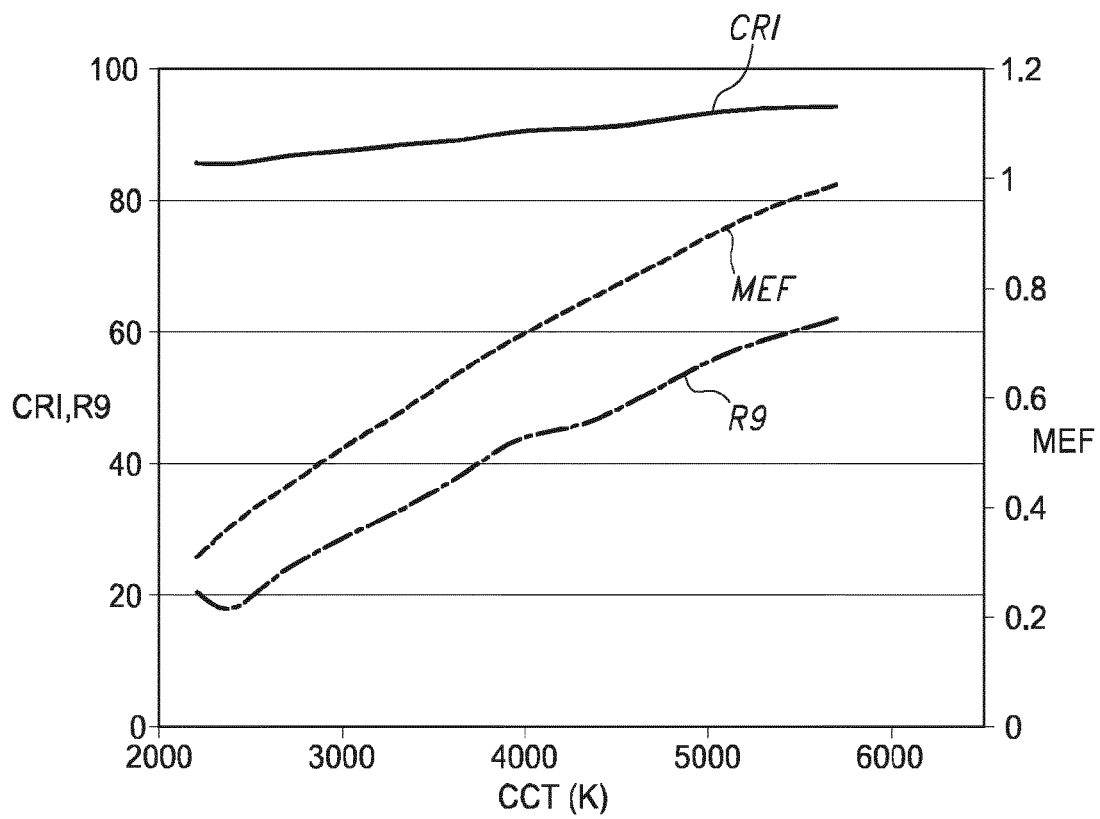
FIG. 3a shows the CRI, R9 and MEF as a function of CCT, for a lamp using 450 nm blue LEDs (reference)

FIG. 3a shows the CRI, R9 and MEF as a function of CCT, for a lamp using 450 nm blue LEDs (reference). A 3-channel solution is used without optimized blue pump LEDs:

Channel 1: 450 nm blue+YAG
Channel 2: 450 nm blue+LuAG
Channel 3: MAlSiN$_3$:Eu(II)

The MEF ratio is 3.2, with a MEF value of 0.31 at 2200 K and a MEF value of 0.91 at 5700 K. Here, the difference in dominant wavelengths of the light sources is zero.

Figure 3B:
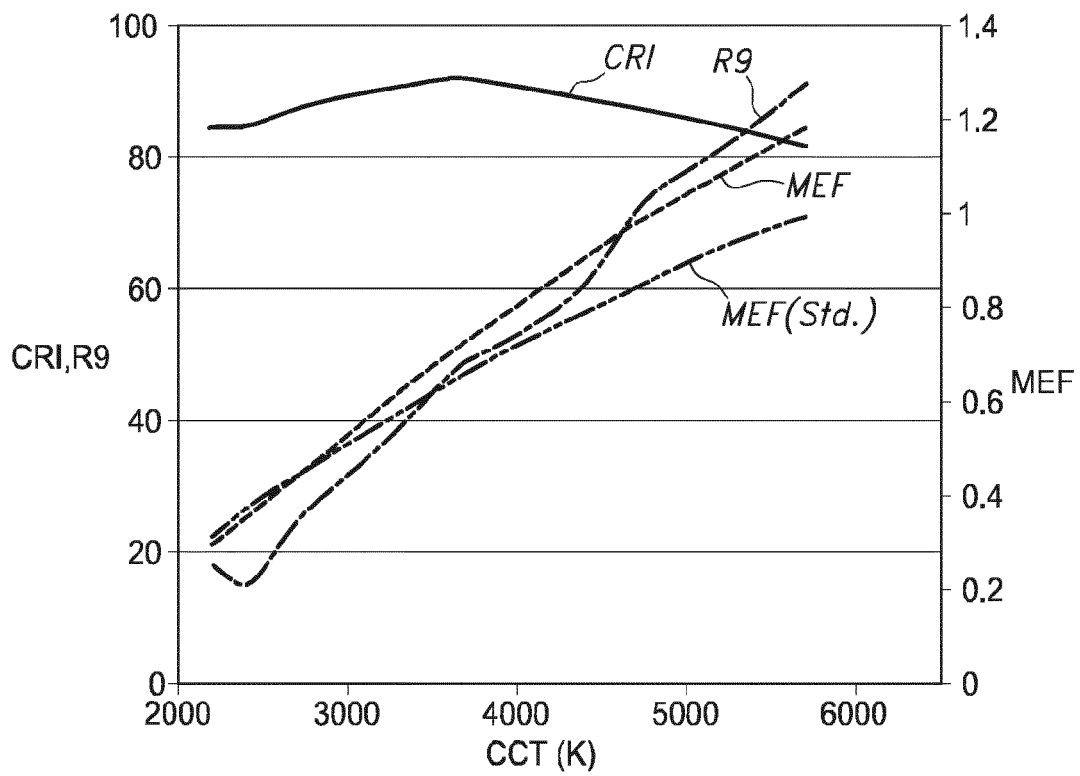
FIG. 3b shows CRI, R9 and MEF as a function of CCT, for a lighting apparatus using a combination of 440 and 462 nm blue LEDs. Dotted blue line: variation in MEF value for standard LED lamp.

FIG. 3b shows CRI, R9 and MEF as a function of CCT, for a lighting apparatus using a combination of 440 and 462 nm blue LEDs. Dotted line: variation in MEF value for standard (std.) LED lamp. Here, an optimized 3-channel solution is chosen: 3-channel solution having optimal blue pump LEDs:

Channel 1: 440 nm blue+YAG
Channel 2: 462 nm blue+LuAG
Channel 3: MAlSiN$_3$:Eu(II) (same as above)

Note that while maintaining a high CRI, the MEF range is much larger, with a MEF at 2200 K of 0.29 and a MEF at 5700 K of 1.18, which is a dynamical spectral MEF range of 4.1 (ratio). Here, the difference in dominant wavelengths of the light sources is about 22 nm.

Figure 3C:
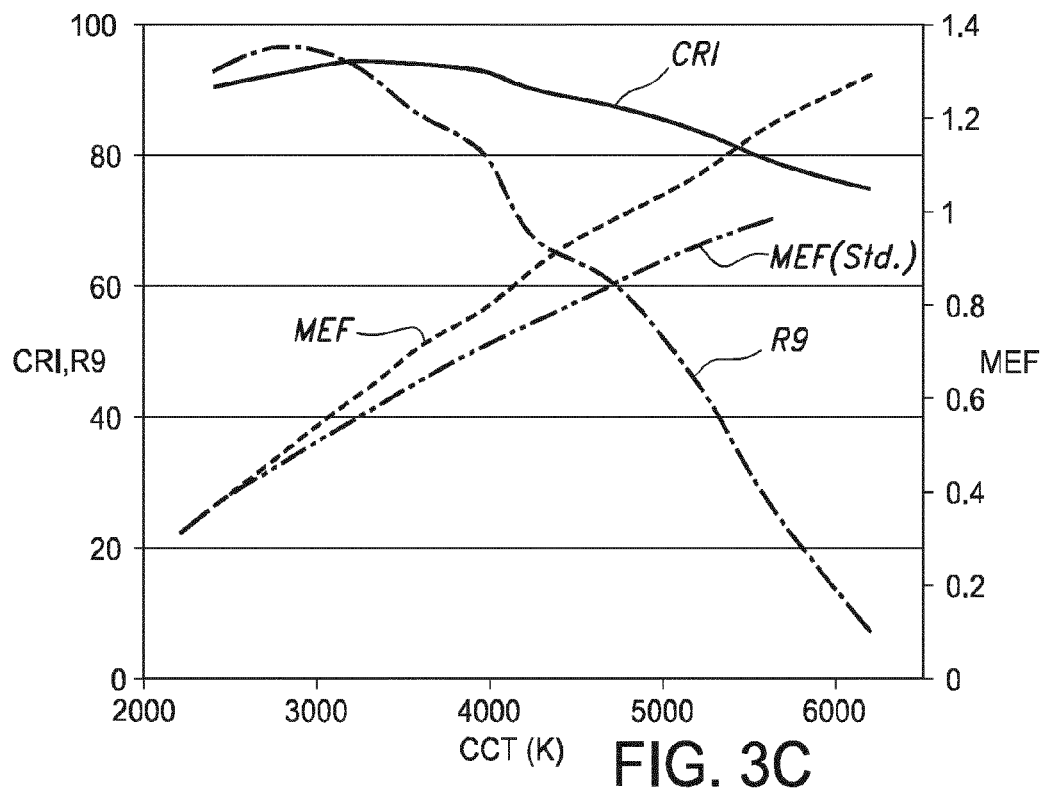
FIG. 3c shows CRI, R9 and MEF as a function of CCT, for a lighting apparatus using a combination of 440 and 462 nm blue LEDs (in combination with direct red LED). Dotted blue line: variation in MEF value for standard LED lamp.

FIG. 3c shows CRI, R9 and MEF as a function of CCT, for a lighting apparatus using a combination of 440 and 462 nm blue LEDs (in combination with direct red LED). Dotted line: variation in MEF value for standard (std.) LED lamp. Here, another embodiment of an optimized 3-channel solution is chosen:

Channel 1: 440 nm blue+YAG
Channel 2: 462 nm blue+LuAG
Channel 3: 613 nm red LED Again, over a fairly large range of correlated color temperatures the CRI is over 80, and a large range of MEF values can be bridged with the lighting apparatus. At 2400 K the MEF value is 0.37 and at 6200 K the MEF value is 1.29, thereby providing a dynamical range of 3.5. Here, the difference in dominant wavelengths of the light sources is about 22 nm.

Figure 4A:
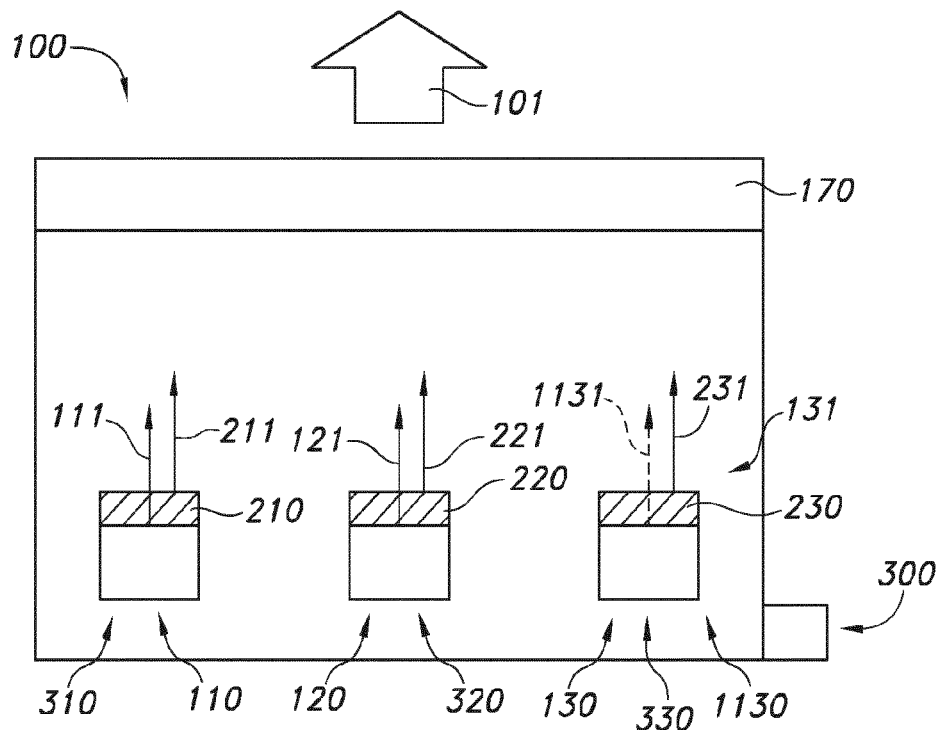
FIGS. 4a-4c schematically depict embodiments of the lighting apparatus.
Figure 4B:
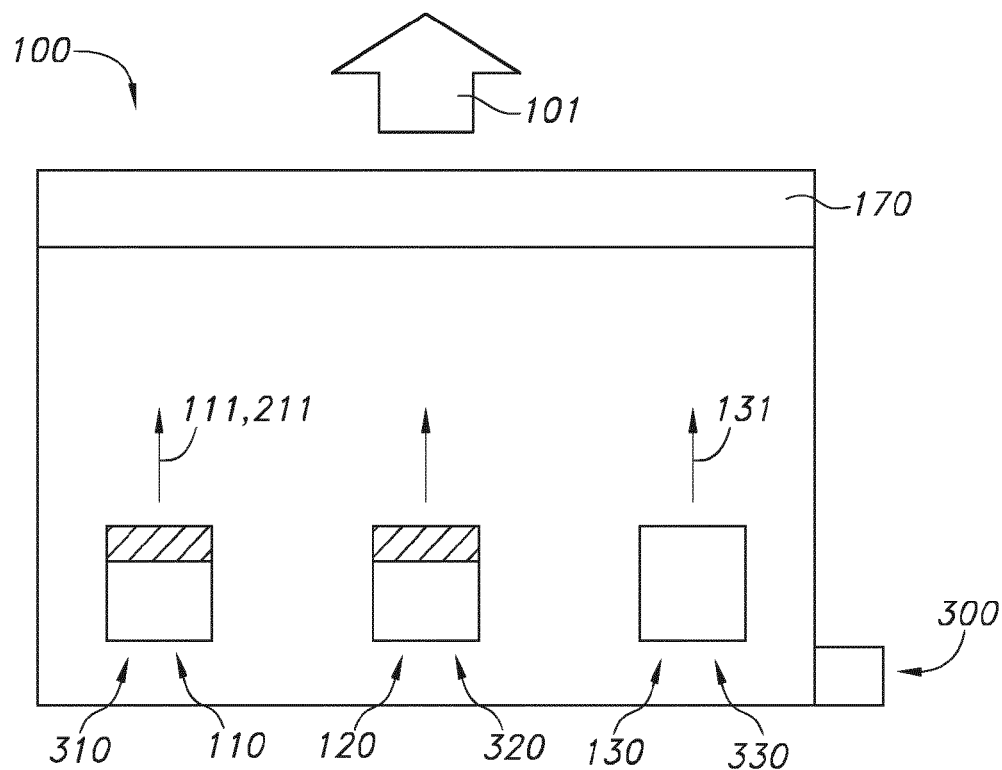
Figure 4C:
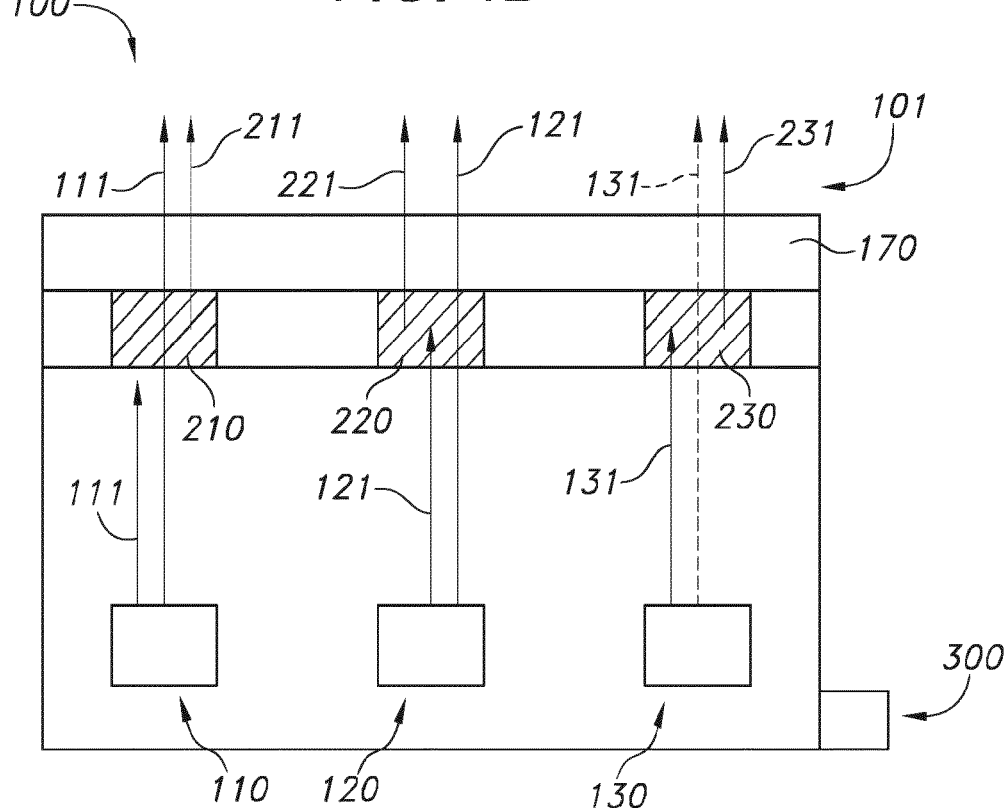

FIGS. 4a-4c schematically depict embodiments of the lighting apparatus. FIG. 4a schematically depicts an embodiment of a lighting apparatus 100 configured to provide white light 101 with a variable correlated color temperature. The lighting apparatus 100 comprises a first light source 110 configured to provide first light source light 111, wherein the first light source light 111 comprises blue light having a first light source dominant wavelength selected from the range of 400-460 nm, wherein the first light source 110 is configured to irradiate a first luminescent material 210 with said first light source light 111, wherein the first luminescent material 210 is configured to convert part of the first light source light 111 into first luminescent material light 211, wherein the first luminescent material light 211 comprises one or more of green and yellow light, and wherein the first luminescent material light 211 has a first luminescent material dominant wavelength.

Further, the lighting apparatus 100 comprises a second light source 120 configured to provide second light source light 121, wherein the second light source light 121 comprises blue light having a second light source dominant wavelength selected from the range of 450-490 nm, wherein the second light source 120 is configured to irradiate a second luminescent material 220 with second light source light 121, and wherein the second luminescent material 220 is configured to convert part of the second light source light 121 into second luminescent material light 221, wherein the second luminescent material light 221 comprises one or more of green and yellow light, and wherein the second luminescent material light 221 has a second luminescent material dominant wavelength.

Yet, the lighting apparatus 100 further comprises a third light source 130 configured to provide red light source light 131.

Further, the lighting apparatus comprises a control unit 300, configured to independently control the first light source 110, the second light source 120 and the third light source 130, to provide said white light 101 having a variable correlated color temperature, wherein said white light 101 comprise (optionally) said red light source light 131 and one or more of (a) said first light source light 111 and said first luminescent material light 211, and (b) said second light source light 121 and said second luminescent material light 221. Hence, especially the control unit is adapted to control the first light source, the second light source and the third light source. Especially, the control unit is thus configured to control the intensity of the first light source light, the second light source light and the third light source light.

In the embodiment of FIG. 4a, the third light source 130 comprises a third solid state light source 1130 configured to provide third solid state light source light 1131, wherein the third solid state light source light 1131 comprises blue light, wherein the third solid state light source 1130 is configured to irradiate a third luminescent material 230 with third solid state light source light 1131, and wherein the third luminescent material 1130 is configured to convert part of the third solid state light source light 1131 into third luminescent material light 231, wherein the third luminescent material light 231 comprises red light. Note that in this embodiment the amount of solid state light source light 1131 is especially low; especially substantially all the solid state light source light 1131 is absorbed by the third luminescent material 230. In an embodiment, the third luminescent material 230 comprises MAlSiN$_3$:Eu(II), wherein M comprises one or more elements selected from the group consisting of barium (Ba), strontium (Sr) and calcium (Ca).

Further, in the embodiment of FIG. 4a the lighting apparatus comprises a first LED package 310 comprising the first light source 110 and the first luminescent material 210, a second LED package 320 comprising the second light source 120 and the second luminescent material 220, and a third LED package 330 comprising the third light source 130 and the third luminescent material 230.

Reference 170 indicates an optional diffusor. Of course, in reality the lighting apparatus 100 will in general comprise a plurality of first light sources, a plurality of second light sources and a plurality of third light sources.

FIG. 4b schematically depicts the same embodiment as of FIG. 4a, but now the third light source 130 comprises a third solid state light source 1130 configured to provide red third solid state light source light 1131 (i.e. without a luminescent material).

FIG. 4c schematically depicts a remote solution. Note that predominantly each light source is associated with the relevant luminescent material. Would the third light source be a red emitting light source without luminescent material, instead of luminescent material a light transmissive part may be included? The light sources are radiationally coupled with the respective luminescent materials.

Figure 5:
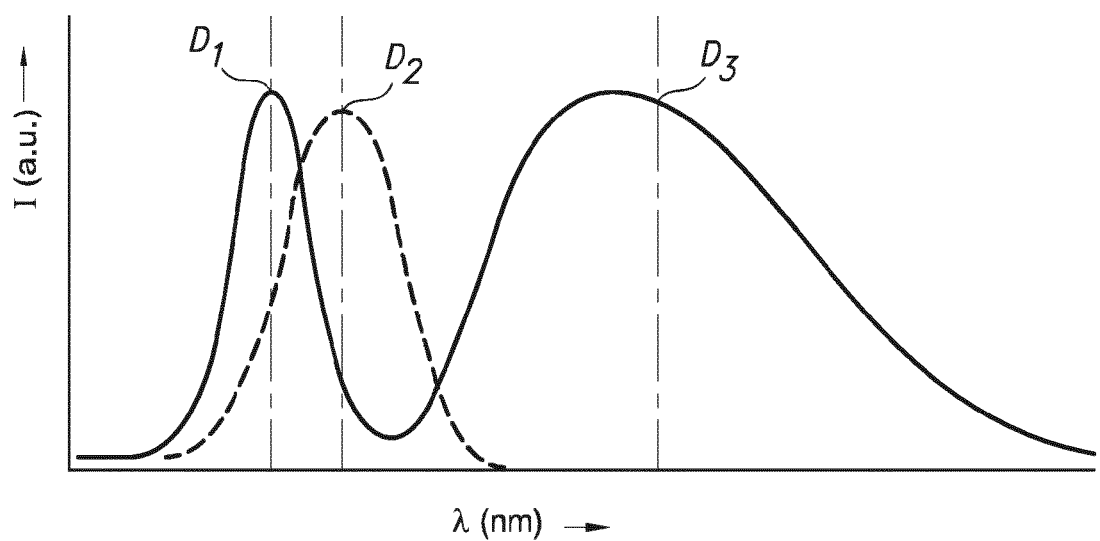
FIG. 5 schematically depicts some aspects of the invention.

FIG. 5 schematically depicts some aspects of the invention. It shows very schematically a blue LED emission with a dominant wavelength D1. For LEDs, the peak maximum and dominant wavelength may substantially be the same. Further, it shows with a dashed curve the melanopsin curve (see FIG. 1). As also this curve is substantially symmetrical, the peak maximum and dominant wavelength may substantially be the same. The emission curve at longer wavelength is substantially asymmetric. Hence, here the dominant wavelength may differ from the peak maximum.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

The invention claimed is:

1. A lighting apparatus configured to provide white light with a variable correlated color temperature, wherein the lighting apparatus comprises:
    a first light source configured to provide first light source light, wherein the first light source light comprises blue light having a first light source dominant wavelength selected from the range of 400-460 nm, wherein the first light source is configured to irradiate a first luminescent material with said first light source light, wherein the first luminescent material is configured to convert part of the first light source light into first luminescent material light, wherein the first luminescent material light comprises one or more of green and yellow light, and wherein the first luminescent material light has a first luminescent material dominant wavelength;
    a second light source configured to provide second light source light, wherein the second light source light comprises blue light having a second light source dominant wavelength selected from the range of 450-490 nm, wherein the second light source is configured to irradiate a second luminescent material with second light source light, and wherein the second luminescent material is configured to convert part of the second light source light into second luminescent material light, wherein the second luminescent material light comprises one or more of green and yellow light, and wherein the second luminescent material light has a second luminescent material dominant wavelength;
    a third light source configured to provide red light source light;
    a control unit, configured to independently control the first light source, the second light source and the third light source, to provide said white light having a variable correlated color temperature, wherein said white light comprises one or more of said first light source light, said first luminescent material light, and said red light source light and, and said second light source light, said second luminescent material light, and said red light source light;
    wherein the second light source dominant wavelength is greater than the first light source dominant wavelength, and wherein the first luminescent material dominant wavelength is greater than the second luminescent material dominant wavelength.

2. The lighting apparatus according to claim 1, wherein the second light source dominant wavelength is less than 475 nm.

3. The lighting apparatus according to claim 1 wherein the first light source light has a dominant wavelength selected from the range of 430-450 nm, and wherein the second light source light has a dominant wavelength selected from the range of 450-475 nm, wherein the difference in dominant wavelengths is in the range of 15-30 nm, wherein the first luminescent material light of the first luminescent material has a dominant wavelength selected from the range of 550-590 nm, and wherein the second luminescent material light of the second luminescent material has a dominant wavelength selected from the range of 520-550 nm.

4. The lighting apparatus according to claim 1, wherein the first luminescent material and the second luminescent material comprises cerium doped garnet luminescent materials.

5. The lighting apparatus according to claim 4, wherein the first luminescent material and the second luminescent material comprise $A_3B_5O_{12}:Ce^{3+}$, wherein A is selected from the group consisting of Y, Gd, Tb and Lu, and wherein B is selected from the group consisting of Al, Ga and Sc, wherein the first luminescent material and the second luminescent material comprise Y and Lu and wherein for the first luminescent material the mole percentage of Y relative to A is larger than for the second luminescent material, and wherein for the second luminescent the mole percentage of Lu relative to A is larger than for the first luminescent material.

6. The lighting apparatus according to claim 1, wherein one or more of the first luminescent material and the second luminescent material comprise quantum dot luminescent materials.

7. The lighting apparatus according to claim 1 wherein the third light source comprises a third solid state light source configured to provide third solid state light source light, wherein the third solid state light source light comprises blue light, wherein the third solid state light source is configured to irradiate a third luminescent material with third solid state light source light, and wherein the third luminescent material is configured to convert part of the third solid state light source light into third luminescent material light, wherein the third luminescent material light comprises red light, and wherein the third luminescent material comprises $MAlSiN_3$: Eu, wherein M comprises one or more elements selected from the group consisting of barium, strontium and calcium.

8. The lighting apparatus according to claim 1 wherein the third light source comprises a third solid state light source configured to provide red third solid state light source light.

9. The lighting apparatus according to claim 1, comprising a first LED package comprising the first light source and the first luminescent material and a second LED package comprising the second light source and the second luminescent material.

10. The lighting apparatus according to claim 1 wherein the control unit is configured to control the first light source, the second light source and the third light source as function of one or more of a time signal and an ambient light sensor.

11. The lighting apparatus according to claim 1 wherein the control unit is further configured to control the melanopsin effectiveness factor of the white light.

12. The lighting apparatus according to claim 11, wherein the control unit is further configured to control the melanopsin effectiveness factor as function of the correlated color temperature of the white light.

13. A method for using the lighting apparatus according to claim 1, comprising providing by the lighting apparatus white light tunable over a correlated color temperature range of at least 2000 K, and providing by the lighting apparatus a variable spectral power distribution in the blue range of the spectrum as function of the correlated color temperature.

14. The method according to claim 13, wherein the lighting apparatus is used for supporting bio rhythm.

15. The method according to claim 13, further comprising providing a first melanopsin effectiveness at a first correlated color temperature and a second melanopsin effectiveness at a second correlated color temperature, wherein the second correlated color temperature is larger than the first correlated color temperature, and wherein the ratio of the second melanopsin effectiveness to the first melanopsin effectiveness is equal to or larger than 3.5.

* * * * *